(12) United States Patent
Kato et al.

(10) Patent No.: US 11,419,880 B2
(45) Date of Patent: *Aug. 23, 2022

(54) URSODEOXYCHOLIC ACID-CONTAINING AGENT FOR TREATING OR PREVENTING PRESBYOPIA

(71) Applicant: SANTEN PHARMACEUTICAL CO., LTD., Osaka (JP)

(72) Inventors: Masatomo Kato, Nara (JP); Tomoko Oda, Nara (JP); Kazutaka Kido, Osaka (JP)

(73) Assignee: Santen Pharmaceutical Co., Ltd., Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 17/546,895

(22) Filed: Dec. 9, 2021

(65) Prior Publication Data

US 2022/0096497 A1    Mar. 31, 2022

Related U.S. Application Data

(63) Continuation of application No. 17/414,285, filed as application No. PCT/JP2019/049352 on Dec. 17, 2019.

(51) Int. Cl.
*A61K 31/575* (2006.01)
*A61P 27/10* (2006.01)
*A61K 9/00* (2006.01)

(52) U.S. Cl.
CPC .......... *A61K 31/575* (2013.01); *A61K 9/0048* (2013.01); *A61P 27/10* (2018.01)

(58) Field of Classification Search
CPC ...... A61K 9/0048; A61K 31/575; A61P 27/10
See application file for complete search history.

(56) References Cited

U.S. PATENT DOCUMENTS

2022/0072012 A1    3/2022  Kato et al.

FOREIGN PATENT DOCUMENTS

| CN | 102178784 A | 9/2011 | |
|---|---|---|---|
| CN | 104083381 A1 | 10/2014 | |
| CN | 106074568 A | 11/2016 | |
| EP | 3581185 A1 | 12/2019 | |
| EP | 3593817 A1 | 1/2020 | |
| GB | 2571644 A * | 9/2019 | .......... A61K 31/575 |
| WO | WO-2010147957 A2 | 12/2010 | |
| WO | WO-2013025840 A1 | 2/2013 | |
| WO | WO-2016029197 A1 * | 2/2016 | .......... A61K 31/404 |
| WO | WO-2018147685 A1 | 8/2018 | |
| WO | WO-2018164113 A1 | 9/2018 | |

OTHER PUBLICATIONS

Abdel-Ghaffer, A., "Ursodeoxycholic acid suppresses the formation of fructose/streptozotocin-induced diabetic cataract in rats," *Fundamental & Clinical Pharmacology*, 32(6):627-640, Wiley-Blackwell Publishing Ltd., United States (Dec. 2018).
English language translation of Patent Search Report for Chinese Application No. 201980081377.5, China National Intellectual Property Administration, China, dated Dec. 6, 2021, 2 pages.
English Translation of International Preliminary Report on Patentability for International Application No. PCT/JP2019/049352, The International Bureau of WIPO, dated Jun. 16, 2021, 5 pages.
English Translation of International Search Report and Written Opinion for International Application PCT/JP2019/049352, Japan Patent Office, Tokyo, dated Mar. 17, 2020, 7 pages.
Garner, W., et al., "Protein Disulfide Levels and Lens Elasticity Modulation: Applications for Presbyopia," *Invest Ophthalmol Vis Sci.*, 57(6):2851-2863, Association for Research in Vision and Ophthalmology, United States (May 2016).
Ide, T., "Definition and Diagnostic Criteria of Presbyopia 2010," *Journal of the Eye*, 28(7):985-988, Medical Aoi Publishing (2011).
Li, M., et al., "Study progress of clinical applications of bear gall powder preparations," *Tianjin Journal of Traditional Chinese Medicine* 32(10):637-640, Tianjin University of Traditional Chinese Medicine, China (Oct. 2015).
Song, S., et al., "Cholesterol-derived bile acids enhances the chaperone activity of α-crystallins," *Cell Stress & Chaperones*, 16(5):475-480, Springer, Germany (2011).
URSO® Tablets 50 mg and 100 mg prescribing label with partial English language translation, Revised Jul. 2019, 7 pages.
Qu, Q. et al., "Clinical Diagnosis and Treatment of Head and Neck Diseases," 2nd ed., pp. 216-217, China Medical Science Press, Beijing, China (Aug. 2014).
English language translation for the Second Office Action for Chinese Patent Application No. 201980081377.5, dated Apr. 28, 2022, The State Intellectual Property Office of China, Beijing, China, 8 pages.

* cited by examiner

*Primary Examiner* — Theodore R. Howell
(74) *Attorney, Agent, or Firm* — Sterne, Kessler, Goldstein & Fox P.L.L.C.

(57) ABSTRACT

The present disclosure provides an agent for treating or preventing eye diseases such as presbyopia, comprising, as an active ingredient, ursodeoxycholic acid or an amide conjugate of ursodeoxycholic acid, or an ester thereof, or a pharmaceutically acceptable salt thereof.

9 Claims, No Drawings

URSODEOXYCHOLIC ACID-CONTAINING AGENT FOR TREATING OR PREVENTING PRESBYOPIA

CROSS-REFERENCE TO RELATED APPLICATIONS

This application is a continuation of U.S. application Ser. No. 17/414,285, filed Jun. 15, 2021, which is a 371 of International Application No. PCT/JP2019/049352, filed Dec. 17, 2019, which claims the benefit of JP Application No. 2018-236717, filed Dec. 18, 2018, each of which are herein incorporated by reference in their entirety.

TECHNICAL FIELD

The present invention relates to an agent for treating or preventing presbyopia, comprising ursodeoxycholic acid or an amide conjugate of ursodeoxycholic acid, or an ester thereof, or a pharmaceutically acceptable salt thereof as an active ingredient.

BACKGROUND ART

Presbyopia is one of aging phenomena of the eye that begins around the age of 40 and is commonly called aged eyes. According to Non-Patent Document 1, presbyopia is defined as a disease state in which the accommodative amplitude decreases with aging (Age-Related Loss of Accommodation). In order to focus on something near or far away, it is necessary for the light that enters the eye to be refracted appropriately as it passes through the lens. Therefore, the eye has the function of adjusting the thickness of the lens such as contraction of the ciliary muscle located near the lens. The ocular tissues involved in the accommodation include lens, Zinn's zonule, lens capsule, and ciliary muscle. However, if the function of the ciliary muscle deteriorates due to aging, or if the lens elasticity (or, viscoelasticity) deteriorates, that is, the lens hardens, it becomes difficult to adjust the thickness of the lens, and it becomes difficult to focus on objects. This condition is presbyopia.

Reading glasses have been used to cope with presbyopia, but there are recent reports of research and development of therapeutic agents for presbyopia. For example, Patent Document 1 discloses that lipoic acid derivatives such as lipoic acid choline ester (alias, EV06, UNR844) are useful for the treatment of presbyopia. And an eye drop comprising lipoic acid choline ester is under clinical development in the United States. Clinical developments of the treatment of presbyopia are also underway for an eye drop comprising AGN-199201 and AGN-190584, an eye drop comprising PRX-100, and an eye drop comprising PresbiDrops (CSF-1). However, the condition of patients with presbyopia is diverse, and an increase in the types of therapeutic agents for eye diseases is still strongly desired so that therapeutic agents can be selected accordingly.

Ursodeoxycholic acid is a compound that promotes bile secretion and inhibits cytokine/chemokine production, and is therefore used in the treatment of liver diseases (Non-Patent Document 2). However, there is no literature reporting relationship between ursodeoxycholic acid and presbyopia treatment.

PRIOR ART DOCUMENT

Patent Document

Patent Document 1: WO 2010/147957

Non-Patent Document

Non-Patent Document 1: *"Atarashii ganka"* [A New Ophthalmology], Vol. 28, No. 7, 985-988, 2011
Non-Patent Document 2: Urso® Tablets 50 mg Urso® Tablets 100 mg Package insert The disclosures of the prior art documents cited herein are hereby incorporated by reference in their entirety.

SUMMARY

Technical Problem

An object of the present application is to provide a new measure for treating or preventing presbyopia, which is a very interesting challenge.

Solution to Problem

As a result of intensive research to solve the above problem, the present inventors have found that ursodeoxycholic acid surprisingly improves lens elasticity, and thereby have reached the present application. Specifically, the present disclosure provides the following aspects of the invention.

[1] An agent for treating or preventing presbyopia comprising, as an active ingredient, ursodeoxycholic acid or an amide conjugate of ursodeoxycholic acid, or an ester thereof, or a pharmaceutically acceptable salt thereof.

[2] An agent for treating or preventing an eye disease accompanied by a decrease in lens elasticity comprising, as an active ingredient, ursodeoxycholic acid or an amide conjugate of ursodeoxycholic acid, or an ester thereof, or a pharmaceutically acceptable salt thereof.

[3] The agent according to [2], wherein the eye disease is accompanied by a decrease in accommodative function of the eye.

[4] An agent for treating or preventing an eye disease accompanied by a decrease in accommodative function of the eye comprising, as an active ingredient, ursodeoxycholic acid or an amide conjugate of ursodeoxycholic acid, or an ester thereof, or a pharmaceutically acceptable salt thereof.

[5] The agent according to any one of [2] to [4], wherein the eye disease is presbyopia.

[6] The agent according to any one of [1] to [5], wherein the agent is for ophthalmic administration.

[7] The agent according to any one of [1] to [6], wherein the agent is an eye drop or an eye ointment.

[8] The agent according to any one of [1] to [7], wherein the amount of ursodeoxycholic acid or an amide conjugate of ursodeoxycholic acid, or an ester thereof, or a pharmaceutically acceptable salt thereof comprised in the agent is 0.00001 to 10% (w/v).

[9] The agent according to any one of [1] to [8], comprising ursodeoxycholic acid, tauroursodeoxycholic acid, glycoursodeoxycholic acid, ursodeoxycholic acid methyl ester, ursodeoxycholic acid ethyl ester, ursodeoxycholic acid n-propyl ester, ursodeoxycholic acid isopropyl ester, ursodeoxycholic acid n-butyl ester, ursodeoxycholic acid isobutyl ester, ursodeoxycholic acid sec-butyl ester, ursodeoxycholic acid tert-butyl ester, ursodeoxycholic acid n-pentyl ester, ursodeoxycholic acid n-hexyl ester, or a pharmaceutically acceptable salt thereof.

[10] The agent according to any one of [1] to [9], comprising ursodeoxycholic acid, tauroursodeoxycholic acid, glycoursodeoxycholic acid, ursodeoxycholic acid methyl ester, ursodeoxycholic acid ethyl ester, ursodeoxycholic acid n-propyl ester, ursodeoxycholic acid isopropyl ester, or a pharmaceutically acceptable salt thereof.

[11] The agent according to any one of [1] to [10], comprising ursodeoxycholic acid or a sodium salt thereof.

[12] The agent according to any one of [1] to [11], further comprising water, and an additive selected from ethyl pyruvate, sodium dihydrogenphosphate monohydrate, disodium hydrogenphosphate, hydroxypropyl methylcellulose, NaCl, and a mixture thereof.

[13] Use of ursodeoxycholic acid or an amide conjugate of ursodeoxycholic acid, or an ester thereof, or a pharmaceutically acceptable salt thereof, in the manufacture of an agent for treating or preventing presbyopia, an eye disease accompanied by a decrease in lens elasticity, or an eye disease accompanied by a decrease in accommodative function of the eye.

[14] Ursodeoxycholic acid or an amide conjugate of ursodeoxycholic acid, or an ester thereof, or a pharmaceutically acceptable salt thereof, for use in the treatment or prevention of presbyopia, an eye disease accompanied by a decrease in lens elasticity, or an eye disease accompanied by a decrease in accommodative function of the eye.

[15] A method for treating or preventing presbyopia, an eye disease accompanied by a decrease in lens elasticity, or an eye disease accompanied by a decrease in accommodative function of the eye, comprising administering to a subject in need thereof an effective amount of ursodeoxycholic acid or an amide conjugate of ursodeoxycholic acid, or an ester thereof, or a pharmaceutically acceptable salt thereof.

Each of the elements described in the above [1] to [15] may be optionally selected and combined.

Advantageous Effects of Invention

The therapeutic or prophylactic agent of the present disclosure can improve the lens elasticity, which is important for lens thickness adjustment, and is therefore useful in the treatment or prevention of eye diseases such as presbyopia etc.

DESCRIPTION OF EMBODIMENTS

Embodiments of the present invention are described in detail below.

The present disclosure provides an agent for treating or preventing presbyopia comprising, as an active ingredient, ursodeoxycholic acid or an amide conjugate of ursodeoxycholic acid, or an ester thereof, or a pharmaceutically acceptable salt thereof (hereinafter sometimes referred to as "the agent of the present invention"). The agent of the present invention may be used to improve lens elasticity. In addition, the agent of the present invention may be used to improve eye accommodation.

Ursodeoxycholic acid is a compound represented by formula (1):

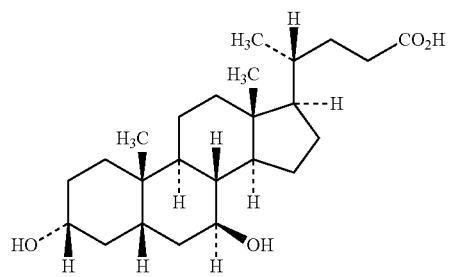

(CAS Registration Number: 128-13-2)), also called ursodiol and 3α,7β-Dihydroxy-5β-cholan-24-oic acid, and sometimes abbreviated as UDCA.

The amide conjugates of ursodeoxycholic acid which may be comprised in the agent of the present invention refer to amide conjugates having a —CO—NH— bond which is formed by dehydration condensation of the carboxyl group of ursodeoxycholic acid with an amino group of an amino compound.

Examples of such amino compound include:

amino acids: for example, alanine, leucine, arginine, lysine, asparagine, methionine, aspartic acid, phenylalanine, cysteine, glutamine, serine, glutamic acid, threonine, glycine, tryptophan, histidine, tyrosine, isoleucine, and valine;

2-aminoadipic acid, 3-aminoadipic acid, 2-aminobutanoic acid, 4-aminobutanoic acid, 2,4-diaminobutanoic acid, 2-aminohexanoic acid, 6-aminohexanoic acid, β-alanine, 2-aminopentanoic acid, 2,3-diaminopropanoic acid, 2-aminopimelic acid, 2,6-diaminopimelic acid, cysteic acid, 2,4-diaminobutanoic acid, 2,6-diaminopimelic acid, 2,3-diaminopropanoic acid, 4-carboxyglutamic acid, homocysteine, homoserine, homoserine lactone, homoserine lactone, 5-hydroxylysine, allohydroxylysine, alloisoleucine, norleucine, norvaline, ornithine, allothreonine, and thyroxine;

amino acid analogs: e.g., taurine.

Examples of the amide conjugates of ursodeoxycholic acid include tauroursodeoxycholic acid and glycoursodeoxycholic acid.

Tauroursodeoxycholic acid is a compound represented by formula (2):

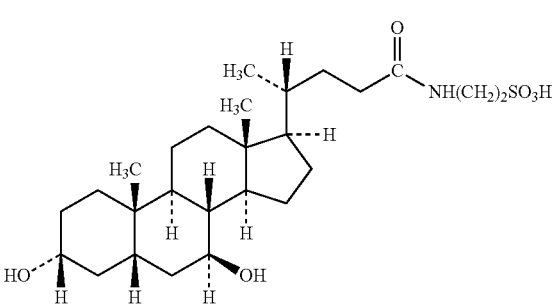

(CAS Registration Number: 14605-22-2), also called 3α,7β-Dihydroxy-5β-cholan-24-oic Acid N-(2-Sulfoethyl) amide, and sometimes abbreviated as TUDCA.

Glycoursodeoxycholic acid is a compound represented by formula (3):

(3)

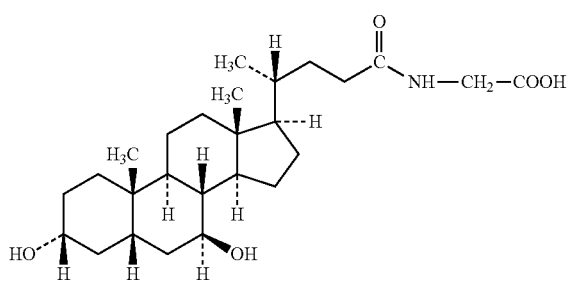

(CAS Registration Number: 64480-66-6), also called N-(3α,7β-Dihydroxy-5(3-cholan-24-oyl)glycine, and sometimes abbreviated as GUDCA.

Examples of the esters of ursodeoxycholic acid which may be comprised in the agent of the present invention include esters which are formed by dehydration condensation of the carboxyl group of ursodeoxycholic acid with a monohydric alcohol having 1 to 6 carbon atoms (preferably 1 to 4 carbon atoms, more preferably 1 to 3 carbon atoms).

Examples of the esters of the amide conjugates of ursodeoxycholic acid which may be comprised in the agent of the present invention include, for example, when the amino compound part has carboxyl group(s) and/or sulfonic acid group(s), esters which are formed by dehydration condensation of the carboxyl group(s) and/or the sulfonic acid group(s) with monohydric alcohol(s) having 1 to 6 carbon atoms (preferably 1 to 4 carbon atoms, more preferably 1 to 3 carbon atoms).

Specific Examples of the esters of ursodeoxycholic acid or the esters of amide conjugates of ursodeoxycholic acid include methyl esters, ethyl esters, n-propyl esters, isopropyl esters, n-butyl esters, isobutyl esters, sec-butyl esters, Cert-butyl esters, n-pentyl esters, and n-hexyl esters. Preferred examples of the ester include methyl esters, ethyl esters, n-propyl esters, and isopropyl esters.

Other examples include carboxylic acid esters which are formed by dehydration condensation of at least one hydroxyl group of ursodeoxycholic acid or an amide conjugate of ursodeoxycholic acid with a carboxylic acid having 1 to 6 carbon atoms (preferably 1 to 4 carbon atoms, more preferably 2 to 3 carbon atoms). Specific examples of the carboxylic acid esters include formate esters, acetate esters, propionate esters, isopropionate esters, butyrate esters, isobutyrate esters, pivalate esters, valerate esters, or isovalerate esters. Preferred examples of the carboxylic acid esters include acetate esters.

Salts of ursodeoxycholic acid, salts of amide conjugates of ursodeoxycholic acid, salts of esters of ursodeoxycholic acid, and salts of esters of amide conjugates of ursodeoxycholic acid, which may be comprised in the agent of the present invention are not particularly limited as long as they are pharmaceutically acceptable salts. Examples of pharmaceutically acceptable salts include, inorganic salts such as hydrochlorides, hydrobromides, hydroiodides, nitrates, sulfates, phosphates, etc.; organic acid salts such as acetates, trifluoroacetates, benzoates, oxalates, malonates, succinates, maleates, fumarates, tartrates, citrates, methanesulfonates, ethanesulfonates, trifluoromethanesulfonates, benzenesulfonates, p-toluenesulfonates, glutamates, aspartates, etc.; metal salts such as sodium salts, potassium salts, calcium salts, and magnesium salts, etc.; inorganic salts such as ammonium salts, etc.; and organic amine salts such as triethylamine salts, guanidine salts, etc. Examples of pharmaceutically acceptable salts include preferably sodium salts and potassium salts.

In the agent of the present invention, ursodeoxycholic acid or amide conjugates of ursodeoxycholic acid, or esters thereof, or pharmaceutically acceptable salts thereof may be in the form of hydrates or solvates.

The amount of ursodeoxycholic acid or an amide conjugate of ursodeoxycholic acid, or an ester thereof, or a pharmaceutically acceptable salt thereof comprised in the agent of the present invention is not particularly limited and may be selected from a wide range depending on dosage forms etc.

For example, the amount of ursodeoxycholic acid or an amide conjugate of ursodeoxycholic acid, or an ester thereof, or a pharmaceutically acceptable salt thereof comprised in the agent of the present invention is 0.00001 to 10% (w/v), preferably 0.0001 to 5% (w/v), more preferably 0.001 to 3% (w/v), even more preferably 0.01 to 2% (w/v), particularly preferably 0.15 to 1.5% (w/v). An example of the lower limit of the amount is 0.00001% (w/v), a preferable example is 0.0001% (w/v), a more preferable example is 0.001% (w/v), a further preferable example is 0.01% (w/v), a particularly preferable example is 0.1% (w/v), a further particularly preferable example is 0.15% (w/v). An example of the upper limit of the amount is 10% (w/v), a preferable example is 5% (w/v), a more preferable example is 3% (w/v), a particularly preferable example is 2% (w/v), a further particularly preferable example is 1.5% (w/v). A preferred range of the amount may be indicated by a combination of the above examples of lower and upper limits.

Further, for example, the amount of ursodeoxycholic acid or an amide conjugate of ursodeoxycholic acid, or an ester thereof, or a pharmaceutically acceptable salt thereof comprised in the agent of the present invention is 0.00001 to 10% (w/w), preferably 0.0001 to 5% (w/w), more preferably 0.001 to 3% (w/w), even more preferably 0.01 to 2% (w/w), particularly preferably 0.15 to 1.5% (w/w). An example of the lower limit of the amount is 0.00001% (w/w), a preferable example is 0.0001% (w/w), a more preferable example is 0.001% (w/w), a further preferable example is 0.01% (w/w), a particularly preferable example is 0.1% (w/w), and a further preferable example is 0.15% (w/w). An example of the upper limit of the amount is 10% (w/w), a preferable example is 5% (w/w), a more preferable example is 3% (w/w), a particularly preferable example is 2% (w/w), and a particularly preferable example is 1.5% (w/w). A preferred range of the amount may be indicated by a combination of the above examples of lower and upper limits.

In one embodiment, the amount of ursodeoxycholic acid or an amide conjugate of ursodeoxycholic acid, or an ester thereof, or a pharmaceutically acceptable salt thereof comprised in the agent of the present invention may be 0.3 to 10% (w/w) (e.g., 0.4 to 5% (w/w), 0.5 to 3% (w/w), 0.6 to 1.5% (w/w), 0.8 to 1.3% (w/w)).

In the present disclosure, "% (w/v)" means the mass (g) of the active ingredient (ursodeoxycholic acid and amide conjugate(s) of ursodeoxycholic acid, and ester(s) thereof, and pharmaceutically acceptable salt(s) thereof) or an additive (surfactant, etc.) comprised in 100 mL of an agent. For example, "0.01% (w/v) of ursodeoxycholic acid" means that the amount of ursodeoxycholic acid comprised in 100 mL of an agent is 0.01 g.

In the present disclosure, "% (w/w)" means the mass (g) of the active ingredient (ursodeoxycholic acid and amide conjugate(s) of ursodeoxycholic acid, and ester(s) thereof, and pharmaceutically acceptable salt(s) thereof) or an additive (surfactant, etc.) comprised in 100 g of an agent. For example, "0.01% (w/w) of ursodeoxycholic acid" means that the amount of ursodeoxycholic acid comprised in 100 g of an agent is 0.01 g.

When ursodeoxycholic acid, an amide conjugate of ursodeoxycholic acid, an ester of ursodeoxycholic acid, or an ester of an amide conjugate of ursodeoxycholic acid are in the form of salt, or in the form of hydrate or solvate (including the form of hydrate or solvate of the salt), the amount of ursodeoxycholic acid or an amide conjugate of ursodeoxycholic acid, or an ester thereof, or a pharmaceutically acceptable salt thereof comprised in the agent may mean the mass of the salt, hydrate, or solvate (including the hydrate or solvate of the salt) added into the agent, or may mean the mass converted as a free form of ursodeoxycholic acid, the amide conjugate of ursodeoxycholic acid or the ester thereof, preferably may mean the mass converted as a free form of ursodeoxycholic acid, the amide conjugate of ursodeoxycholic acid, or the ester thereof.

In this disclosure, the term "presbyopia" means a symptom/disease that is determined to be presbyopia based on general criteria used by a physician or professional.

For example, diagnostic criteria for presbyopia include:

Decreased near vision is noticed as a subjective symptom in a binocular vision test, and a binocular daily life visual acuity, which is a binocular distant visual acuity measured under the same condition as daily life, is less than 0.4 at 40 cm distance (clinical presbyopia); and/or With or without subjective symptoms, under unilateral best-correction where a corrected visual acuity of one eye is equal to or more than 1.0 (decimal visual acuity), accommodative amplitude is less than 2.5 Diopters" (medical presbyopia).

However, if an accommodometer etc. is not available, a simple criterion wherein a visual acuity at 40 cm is less than 0.4 may be used.

In the present disclosure, the term "an eye disease accompanied by a decrease in lens elasticity" refers to an eye disease considered in the field of ophthalmology to be accompanied by a decrease in lens elasticity, including, for example, presbyopia (e.g., presbyopia due to aging), and a hardening of the lens induced by drugs and the like.

In the present disclosure, the term "accommodation function of the eye" refers to an eye function that automatically focuses on distant and/or near objects. The term "an eye disease accompanied by a decrease in accommodative function of the eye" refers to an eye disease considered in the field of ophthalmology to be accompanied by a decrease in accommodative function of the eye, including, for example, presbyopia (e.g., presbyopia due to aging), and a hardening of the lens induced by drugs etc., and decreased accommodation function induced by seeing near objects for a long time.

The efficacy of the agent of the present invention may be evaluated, for example, as an increase in "accommodative amplitude of the eye".

The accommodative amplitude of the eye can be measured as a Diopter (D) which can be determined by the following expression 1:

$$\text{Diopter } (D) = 1/\text{Near Point Distance } (m) \quad \text{(Expression 1)}.$$

In general, the accommodative amplitude of the eye is greater than 10 diopters at 10 years, then gradually decreases to about 3 diopters at about 45 years and is almost lost at about 60 years. When the accommodative amplitude decreases to about 3 diopters, it becomes difficult to focus on near objects (about 30 cm) in daily life, and subjective symptoms of presbyopia appear.

The efficacy of the agent of the present invention may be evaluated, for example, as an improvement in "visual acuity". The visual acuity can be measured as near visual acuity (uncorrected visual acuity, distance-corrected near visual acuity, corrected visual acuity) and can be measured by using decimal visual acuity, fractional visual acuity, or log MAR.

In general, when near visual acuity which is defined to be measured at about 40 cm decreases to below 0.4, it causes difficulty in seeing near objects, and subjective symptoms of presbyopia appear. The agent of the present invention may be used to improve near visual acuity (e.g., distance-corrected near visual acuity).

The agent of the invention may begin to exhibit an efficacy within one year, preferably within six months, more preferably within one month, more preferably within one week, and most preferably within one day after the administration. Further, once an efficacy is exerted, the efficacy may be exerted continuously until after one day, preferably until after one week, more preferably until after one month, more preferably until after six months, particularly preferably until after one year, and most preferably until after three years.

The agent of the present invention may be administered, for example, so as to increase the accommodative amplitude of the eye by at least about 0.5 diopters (preferably at least about 1 diopter, more preferably at least about 1.5 diopters, more preferably at least about 2 diopters, even more preferably at least about 3 diopters, and still more preferably at least about 4 diopters, particularly preferably at least about 5 diopters, and still more preferably at least about 10 diopters).

The agent of the present invention may be administered, for example, so as to increase distance-corrected near visual acuity (DCNVA) by at least about 0.5 log MAR (preferably about at least 1.0 log MAR, more preferably about at least 1.5 log MAR, even more preferably about 2.0 log MAR, even more preferably about 3.0 log MAR, particularly preferably about 4.0 log MAR, particularly preferably about 5.0 log MAR, and even more preferably about 6.0 log MAR).

The term "distance-corrected near visual acuity" generally refers to near visual acuity measured with distance visual acuity corrected to 0.0 log MAR (decimal visual acuity of 1.0 or more).

The agent of the present invention may be administered, for example, so as to restore the accommodative amplitude of the eye to at least about 0.5 diopters (preferably at least about 1 diopter, more preferably at least about 1.5 diopters, more preferably at least about 2 diopters, more preferably at least about 3 diopters, particularly preferably at least about 4 diopters, particularly preferably at least about 5 diopters, and still more preferably at least about 10 diopters).

The agent of the present invention may be administered, for example, so as to restore the distance-corrected near visual acuity (DCNVA) to at least about 0.5 log MAR (preferably at least about 1.0 log MAR, more preferably at least about 1.5 log MAR, even more preferably about 2.0 log MAR, even more preferably about 3.0 log MAR, particularly preferably about 4.0 log MAR, particularly preferably about 5.0 log MAR, and even more preferably about 6.0 log MAR).

In the present disclosure, the treatment or prevention of presbyopia includes increasing an elasticity of the lens, improving an ability to adjust a thickness of lens, and/or improving an accommodative function of the eye.

Although subjective symptoms of presbyopia generally appear at about 45 years of age as mentioned above, age-related decline in eye accommodation has been progressing since teens. The agent of the present invention may be used after the subjective symptoms of presbyopia appear, and may be used to prevent and/or delay progression of presbyopia before the subjective symptoms of presbyopia appear.

The subjects of administration of the agent of the present invention are mammals including livestock such as cattle and pigs; rabbits, monkeys, dogs, cats, and humans, preferably humans.

In this disclosure, "treatment (treating)" and "prevention (preventing)" may include, in addition to treating and preventing a disease, alleviating symptoms of the disease, delaying progression of the disease, suppressing symptoms of the disease, and inducing improvement in symptoms of the disease.

The agent of the present invention may be administered orally or parenterally (e.g., ocularly, nasally, transdermally, transmucosally, by injection, etc.). The agent of the present invention may be prepared in the usual manner in the art by mixing the active ingredient with, for example, one or more pharmaceutically acceptable additives, for example, in the form of oral preparations such as tablets, capsules, granules, powders, lozenges, syrups, emulsions, suspensions, and the like, or parenteral preparations such as eye drops, ophthalmic ointments, injections, suppositories, nasal preparations, and the like. Preferred formulations of the agent of the present invention include eye drops (e.g., ophthalmic suspensions) and eye ointments from the viewpoint of greater efficacy of the agents of the invention.

Pharmaceutically acceptable additives that may be comprised in the agent of the present invention are not particularly limited and may be selected as appropriate according to the route of administration, formulation, etc. Examples of such pharmaceutically acceptable additives include, for example, surfactants, buffers, tonicity agents, stabilizers, preservatives, antioxidants, thickeners, solubilizing agents, suspending agents, bases, solvents, pH adjusters, excipients, disintegrating agents, binders, fluidizers, lubricants, preservatives, antioxidants, coloring agents, sweetening agents, and the like.

When the agent of the present invention is an eye drop, examples of additives that may be used include surfactants, buffers, tonicity agents, stabilizers, preservatives, antioxidants, thickeners, solvents, pH adjusters, and the like.

Examples of surfactants include cationic surfactants, anionic surfactants, nonionic surfactants and the like.

When a surfactant is added to the agent of the present invention, the amount of the surfactant comprised in the agent may be appropriately adjusted depending on the type of the surfactant, etc., and is preferably, for example, 0.01 to 1% (w/v).

Examples of buffers include phosphoric acid or salts thereof, which may be hydrates or solvates thereof.

Examples of the phosphoric acid or salts thereof include phosphoric acid, trisodium phosphate, sodium dihydrogenphosphate, sodium hydrogen phosphate (disodium hydrogenphosphate) and the like, which may be hydrates thereof.

When a buffer is added to the agent of the present invention, the amount of the buffer comprised in the agent may be appropriately adjusted depending on the type of the buffer, etc., but for example, 0.001 to 10% (w/v) is preferable, and 0.01 to 5% (w/v) is more preferable. Two or more kinds of buffers may be used together.

Examples of tonicity agents include ionic tonicity agents and nonionic tonicity agents. Examples of the ionic tonicity agents include sodium chloride and the like.

When a tonicity agent is added to the agent of the present invention, the amount of the tonicity agent comprised in the agent may be appropriately adjusted according to the type of the tonicity agent or the like, but for example, 0.001 to 10% (w/v) is preferable, and 0.01% to 5% (w/v) is more preferable.

Examples of thickeners include hydroxypropyl methylcellulose and the like.

When a thickener is added to the agent of the present invention, the amount of the thickener may be appropriately adjusted according to the type of the thickener or the like, but for example, 0.001 to 5% (w/v) is preferable, and 0.01% to 3% (w/v) is more preferable.

When the agent of the present invention is an aqueous formulation (e.g., eye drops), the pH is preferably 4 to 8 and more preferably 5 to 7.

Examples of solvents include water, physiological saline and the like.

Examples of the agent of the present invention which is an aqueous preparation (e.g., eye drop) include aqueous preparations comprising ursodeoxycholic acid or an amide conjugate of ursodeoxycholic acid, or an ester thereof, or a pharmaceutically acceptable salt thereof, water, and an additive selected from ethyl pyruvate, sodium dihydrogenphosphate monohydrate ($NaH_2PO_4H_2O$), disodium hydrogenphosphate ($Na_2HPO_4$), hydroxypropyl methylcellulose, NaCl, and a mixture thereof. Here, said "a mixture thereof" means any combination of the listed specific additives.

As used herein, the term "an effective amount" is the amount of the active ingredient required to provide a patient benefit in the symptoms of a disease.

A dosage and administration of the agent of the present invention is not particularly limited as long as the dosage and administration are sufficient to achieve the desired medicinal effect, and may be appropriately selected according to the symptoms of the disease, the age and weight of the patient, the dosage form of the agent, etc.

For example, in the case of eye drops, a single dose of 1 to 5 drops (preferably 1 to 3 drops, more preferably 1 to 2 drops, particularly preferably 1 drop) may be instilled 1 to 4 times per day (preferably 1 to 3 times per day, more preferably 1 to 2 times per day, particularly preferably once per day), every day or at an interval of from one day to one week. The "one drop" is usually about 0.01 to about 0.1 mL, preferably about 0.015 to about 0.07 mL, more preferably about 0.02 to about 0.05 mL, and particularly preferably about 0.03 mL.

In one embodiment, the agent of the present invention have an immediate effect on presbyopia, an eye disease accompanied by a decrease in lens elasticity, or an eye disease accompanied by a decrease in accommodative function of the eye, for example, compared to EV06.

The duration of administration of the agent of the present invention may be determined by a physician or professional.

In one embodiment, the agent of the present invention may be an ophthalmic administration agent such as an eye drop (e.g., a suspension) and an eye ointment, and may be used continuously for at least 2 days, at least 3 days, at least 7 days, at least 10 days.

In one embodiment, the agent of the present invention may be administered at least once (e.g., at least twice, at least three times) a day.

In one embodiment, the agent of the present invention, when administered to the eye, may be less irritating to the eye while having an effect on presbyopia, an eye disease accompanied by a decrease in lens elasticity, or an eye disease accompanied by a decrease in accommodative function of the eye.

EXAMPLES

The results of pharmacological tests are shown below for a better understanding of the present invention and are not intended to limit the scope of the present invention.
[Pharmacological Test 1]
The effect of lipoic acid choline ester (EV06) on the lens elasticity was examined. The tests were conducted with reference to the methods described in InvestOphthalmol Vis Sci, 57, 2851-2863, 2016. EV06 is a compound represented by the following formula (2):

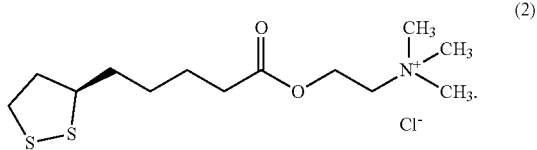 [SMILES: C[N+](C)(C)CCOC(=O)CCCC[C@@H]1CCSS1 ; [Cl-]]

(2)

(Preparation of Test Sample)
1) Preparation of Vehicle
A vehicle comprising 0.1% (w/v) of ethyl pyruvate, 0.269% (w/v) of sodium dihydrogenphosphate monohydrate (NaH$_2$PO$_4$H$_2$O), 0.433% (w/v) of disodium hydrogenphosphate (Na$_2$HPO$_4$), 0.2% (w/v) of hydroxypropyl methylcellulose, and 0.5% (w/v) of NaCl was prepared.
2) Preparation of EV06 Sample
EV06 was sonicated with the addition of the vehicle to prepare a 5% (w/v) suspension. The resulting 5% (w/v) suspension was diluted with the vehicle to prepare a 1.5% (w/v) solution. Further, the resulting 1.5% (w/v) solution was diluted with the vehicle to prepare a 0.5% (w/v) solution. The total amount of each sample to be used in one day was prepared before use.
(Test Method)
1) Each test sample (2.5 μL/eye) was instilled into the right eye of 8-month-old C57BL/6J mice with a Pipetman 3 times per day (around 9:00, 13:00 and 17:00) for 15 to 17 days.
2) After the final instillation, the mice were euthanized by carbon dioxide inhalation, and then the eyeballs were extracted and rinsed with Hank's balanced salt solution (HBSS).
3) The sclera near the optic nerve was cut with a razor, the lens was removed through the incision, and the removed lens was immersed in HESS.
4) The lens was placed on a glass slide, and an all-in-one fluorescence microscope BZ-9000 (Keyence) was used to capture an image of the lens (Image a).
5) Next, one cover glass (Corning® 22×22 mm Square) was placed on the lens, and an image in which the thickness of the lens changed due to the weight was similarly captured (Image b).
6) A change in the lens diameter was calculated from Equation 1 wherein the lens diameter of Image a is subtracted from the lens diameter of Image b, as described below. Then, the lens elasticity improvement of each sample group compared with the vehicle control group was calculated from Equation 2 described below.

The mean of the vehicle control group was based on 6 eyes and the mean of each EV06 sample group was based on 12 eyes.

Change in lens diameter=Lens diameter in Image $b$ of each test sample−Lens diameter in Image $a$ of each test sample   (Equation 1)

Lens elasticity improvement of each sample group=Mean change in lens diameter of each EV06 sample group−Mean change in lens diameter of Vehicle control group   (Equation 2)

(Results)
The results are shown in Table 1.

TABLE 1

| | Lens elasticity improvement (μm) |
|---|---|
| 0.5% EV06 sample | 28.8 |
| 1.5% EV06 sample | 47.3 |
| 5% EV06 sample | 48.7 |

As shown in Table 1, all of the 0.5%, 1.5%, and 5% EV06 groups showed the increased lens diameter compared with the vehicle control group, which confirms that EV06 has an elasticity improving effect.
[Pharmacological Test 2]
The effect of sodium ursodeoxycholate on the lens elasticity was examined.
(Preparation of Test Sample)
1) Preparation of Vehicle
A vehicle comprising 0.1% (w/v) of ethyl pyruvate, 0.269% (w/v) of sodium dihydrogenphosphate monohydrate (NaH$_2$PO$_4$H$_2$O), 0.433% (w/v) of disodium hydrogenphosphate (Na$_2$HPO$_4$), 0.2% (w/v) of hydroxypropyl methylcellulose, 0.5% (w/v) of NaCl was prepared.
2) Preparation of Sodium Ursodeoxycholate Sample
Sodium ursodeoxycholate was sonicated with the addition of the vehicle to prepare a 1.5% (w/v) suspension. The resulting 1.5% (w/v) suspension was diluted with the vehicle to prepare a 0.5% (w/v) suspension. Further, the resulting 0.5% (w/v) suspension was diluted with the vehicle to prepare a 0.15% (w/v) suspension. The total amount of each sample to be used in one day was prepared before use.
3) Preparation of EV06 Sample
EV06 was sonicated with the addition of the vehicle to prepare a 1.5% (w/v) solution. The total amount of the sample to be used in one day was prepared before use.
(Test Method)
1) Each test sample (2.5 μL/eye) was instilled into the right eye of 8-month-old C57BL/6J mice with a Pipetman 3 times per day (around 9:00, 13:00 and 17:00) for 12 to 15 days.
2) After the final instillation, the mice were euthanized by carbon dioxide inhalation, and then the eyeballs were extracted and rinsed with Hank's balanced salt solution (HBSS).
3) The sclera near the optic nerve was cut with a razor, the lens was removed through the incision, and the removed lens was immersed in HBSS.
4) The lens was placed on a glass slide, and an all-in-one fluorescence microscope BZ-9000 (Keyence) was used to capture an image of the lens (Image a).
5) Next, one cover glass (Corning® 22×22 mm Square) was placed on the lens, and an image in which the thickness of the lens changed due to the weight was similarly captured (Image b).
6) A change in the lens diameter was calculated from Equation 1 wherein the lens diameter of Image a is subtracted from the lens diameter of Image b, as described below. Then, the lens elasticity improvement of each sample group compared with the vehicle control group was calculated from Equation 2 described below. The mean of the vehicle control group was based on 5 eyes, the mean of each sodium ursodeoxycholate sample group was based on 10 eyes, and the mean of the EV06 sample group was based on 10 eyes.

Change in lens diameter=Lens diameter in Image b of each test sample−Lens diameter in Image a of each test sample (Equation 1)

Lens elasticity improvement of each sample group=Mean change in lens diameter of each Test sample group−Mean change in lens diameter of Vehicle control group (Equation 2)

(Results)
The results are shown in Table 2.

TABLE 2

|  | Lens elasticity improvement(μm) |
| --- | --- |
| 0.15% sodium ursodeoxycholate sample | 26.5 |
| 0.5% sodium ursodeoxycholate sample | 34.8 |
| 1.5% sodium ursodeoxycholate sample | 44.7 |
| 1.5% EV06 sample | 38.2 |

As shown in Table 2, all of the 0.15%, 0.5%, and 1.5% sodium ursodeoxycholate sample groups showed a potent lens elasticity improving effect. The lens elasticity improving effect of the 1.5% sample group was stronger than that of EV06 at the same concentration.

[Pharmacological Test 3]
The effect of ursodeoxycholic acid (free form) on the lens elasticity was examined.
(Preparation of Test Sample)
1) Preparation of Vehicle
A vehicle comprising 0.1% (w/v) of ethyl pyruvate, 0.269% (w/v) of sodium dihydrogenphosphate monohydrate (NaH$_2$PO$_4$H$_2$O), 0.433% (w/v) of disodium hydrogenphosphate (Na$_2$HPO$_4$), 0.2% (w/v) of hydroxypropyl methylcellulose, and 0.5% (w/v) of NaCl was prepared.
2) Preparation of Ursodeoxycholic Acid Sample
Ursodeoxycholic acid was sonicated with the addition of the vehicle to prepare a 1.5% (w/v) suspension. The resulting 1.5% (w/v) suspension was diluted with the vehicle to prepare a 0.5% (w/v) suspension. Further, the resulting 0.5% (w/v) suspension was diluted with the vehicle to prepare a 0.15% (w/v) suspension. The total amount of each sample to be used in one day was prepared before use.
3) Preparation of EV06 Sample
EV06 was sonicated with the addition of the vehicle to prepare a 1.5% (w/v) solution. The total amount of the sample to be used in one day was prepared before use.
(Test Method)
1) Each test sample (2.5 μL/eye) was instilled into the right eye of 8-month-old C57BL/6J mice with a Pipetman 3 times per day (around 9:00, 13:00 and 17:00) for 12 to 15 days.
2) After the final instillation, the mice were euthanized by carbon dioxide inhalation, and then the eyeballs were extracted and rinsed with Hank's balanced salt solution (HESS).
3) The sclera near the optic nerve was cut with a razor, the lens was removed through the incision, and the removed lens was immersed in HESS.
4) The lens was placed on a glass slide, and an all-in-one fluorescence microscope BZ-9000 (Keyence) was used to capture an image of the lens (Image a).
5) Next, one cover glass (Corning® 22×22 mm Square) was placed on the lens, and an image in which the thickness of the lens changed due to the weight was similarly captured (Image b).
6) A change in the lens diameter was calculated from Equation 1 wherein the lens diameter of Image a is subtracted from the lens diameter of Image b, as described below. Then, the lens elasticity improvement of each sample group compared with the vehicle control group was calculated from Equation 2 described below. The mean of the vehicle control group was based on 5 eyes, the mean of each ursodeoxycholic acid sample group was based on 10 eyes, and the mean of the EV06 sample group was based on 10 eyes.

Change in lens diameter=Lens diameter in Image b of each test sample−Lens diameter in Image a of each test sample (Equation 1)

Lens elasticity improvement of each sample group=Mean change in lens diameter of each Test sample group−Mean change in lens diameter of Vehicle control group (Equation 2)

(Results)
The results are shown in Table 3.

TABLE 3

|  | Lens elasticity improvement(μm) |
| --- | --- |
| 0.15% ursodeoxycholic acid sample | 31.8 |
| 0.5% ursodeoxycholic acid sample | 39.4 |
| 1.5% ursodeoxycholic acid sample | 59.9 |
| 1.5% EV06 sample | 42.5 |

As shown in Table 3, all of the 0.15%, 0.5%, and 1.5% sodium ursodeoxycholate sample groups showed a potent lens elasticity improving effect. The lens elasticity improving effect of the 1.5% sample group was stronger than that of EV06 at the same concentration.

[Pharmacological Test 4]
The effect of once-daily instillation of ursodeoxycholic acid for 2 weeks on the lens elasticity was examined.
(Preparation of Test Sample)
1) Preparation of Vehicle
A vehicle comprising 0.1% (w/v) of ethyl pyruvate, 0.269% (w/v) of sodium dihydrogenphosphate monohydrate (NaH$_2$PO$_4$H$_2$O), 0.433% (w/v) of disodium hydrogenphosphate (Na$_2$HPO$_4$), 0.2% (w/v) of hydroxypropyl methylcellulose, 0.5% (w/v) of NaCl was prepared.
2) Preparation of Ursodeoxycholic Acid Sample
Ursodeoxycholic acid was sonicated with the addition of the vehicle to prepare a 3.0% (w/v) suspension. The resulting 3.0% (w/v) suspension was diluted with the vehicle to prepare a 1.0% (w/v) suspension. Further, the resulting 1.0% (w/v) suspension was diluted with the vehicle to prepare a 0.3% (w/v) suspension. The total amount of each sample to be used in one day was prepared before use.
3) Preparation of EV06 Sample
EV06 was sonicated with the addition of the vehicle to prepare a 1.5% (w/v) solution. The total amount of the sample to be used in one day was prepared before use.

(Test Method)
1) Each test sample (2.5 µL/eye) was instilled into the right eye of 8-month-old C57BL/6J mice with a Pipetman once per day (QD; around 9:00), twice per day (BID; around 9:00 and 17:00), or 3 times per day (TID; around 9:00, 13:00 and 17:00) for 14 days.
2) After the final instillation, the mice were euthanized by carbon dioxide inhalation, and then the eyeballs were extracted and rinsed with Hank's balanced salt solution (HBSS).
3) The sclera near the optic nerve was cut with a razor, the lens was removed through the incision, and the removed lens was immersed in HBSS.
4) The lens was placed on a glass slide, and an all-in-one fluorescence microscope BZ-9000 (Keyence) was used to capture an image of the lens (Image a).
5) Next, one cover glass (Corning® 22×22 mm Square) was placed on the lens, and an image in which the thickness of the lens changed due to the weight was similarly captured (Image b).
6) A change in the lens diameter was calculated from Equation 1 wherein the lens diameter of Image a is subtracted from the lens diameter of Image b, as described below. Then, the lens elasticity improvement of each sample group compared with the vehicle control group was calculated from Equation 2 described below. The mean of the vehicle control group was based on 5 eyes, the mean of each ursodeoxycholic acid sample group was based on 10 eyes, and the mean of each EV06 sample group was based on 10 eyes.

Change in lens diameter=Lens diameter in Image $b$ of each test sample–Lens diameter in Image $a$ of each test sample    (Equation 1)

Lens elasticity improvement of each sample group=Mean change in lens diameter of each Test sample group–Mean change in lens diameter of Vehicle control group    (Equation 2)

(Results)
The results are shown in Table 4.

TABLE 4

|  | Lens elasticity improvement (µm) |
| --- | --- |
| 0.3% ursodeoxycholic acid sample (QD) | 2.8 |
| 1% ursodeoxycholic acid sample (QD) | 28.1 |
| 3% ursodeoxycholic acid sample (QD) | 30.4 |
| 1.5% EV06 sample (QD) | −3.6 |
| 1.5% EV06 sample(BID) | 15.7 |
| 1.5% EV06 sample(TID) | 29.5 |

As shown in Table 4, 1% ursodeoxycholic acid sample and 3% ursodeoxycholic acid sample caused a potent lens elasticity improvement when they were instilled once-daily while 1.5% EV06 sample instilled once-daily had no effect, which indicates that ursodeoxycholic acid has a more potent lens elasticity improvement effect compared with EV06.

[Pharmacological Test 5]
The effect of 1% ursodeoxycholic acid instilled once-daily for 1, 3, 7, 10, or 14 days on the lens elasticity was examined.
(Preparation of Test Sample)
1) Preparation of Vehicle
A vehicle comprising 0.1% (w/v) of ethyl pyruvate, 0.269% (w/v) of sodium dihydrogenphosphate monohydrate ($NaH_2PO_4H_2O$), 0.433% (w/v) of disodium hydrogenphosphate ($Na_2HPO_4$), 0.2% (w/v) of hydroxypropyl methylcellulose, 0.5% (w/v) of NaCl was prepared.
2) Preparation of 1% Ursodeoxycholic Acid Sample
Ursodeoxycholic acid was sonicated with the addition of the vehicle to prepare a 1.0% (w/v) suspension. The total amount of the sample to be used in one day was prepared before use.
(Test Method)
1) The test sample (2.5 µL/eye) was instilled into both eyes of 8-month-old C57BL/6J mice with a Pipetman once per day (QD; around 13:30) for 1, 3, 7, 10, or 14 days.
2) Twenty-four hours after the final instillation, the mice were euthanized by carbon dioxide inhalation, and then the eyeballs were extracted and rinsed with Hank's balanced salt solution (HBSS).
3) The sclera near the optic nerve was cut with a razor, the lens was removed through the incision, and the removed lens was immersed in HBSS.
4) The lens was placed on a glass slide, and an all-in-one fluorescence microscope BZ-9000 (Keyence) was used to capture an image of the lens (Image a).
5) Next, one cover glass (Corning® 22×22 mm Square) was placed on the lens, and an image in which the thickness of the lens changed due to the weight was similarly captured (Image b).
6) A change in the lens diameter was calculated from Equation 1 wherein the lens diameter of Image a is subtracted from the lens diameter of Image b, as described below. Then, the lens elasticity improvement of each sample group compared with the vehicle control group was calculated from Equation 2 described below. Each mean of the untreated group and each ursodeoxycholic acid sample group was based on 9 or 10 eyes.

Change in lens diameter=Lens diameter in Image $b$ of each test sample–Lens diameter in Image $a$ of each test sample    (Equation 1)

Lens elasticity improvement of each sample group=Mean change in lens diameter of each Test sample group–Mean change in lens diameter of Untreated group    (Equation 2)

(Results)
The results are shown in Table 5.

TABLE 5

|  | Lens elasticity improvement (µm) |
| --- | --- |
| 1% ursodeoxycholic acid sample (1 day) | 9.6 |
| 1% ursodeoxycholic acid sample (3 days) | 21.1 |
| 1% ursodeoxycholic acid sample (7 days) | 27.4 |
| 1% ursodeoxycholic acid sample (10 days) | 38.1 |
| 1% ursodeoxycholic acid sample (14 days) | 34.2 |

As shown in Table 5, the 1% ursodeoxycholic acid sample instilled once-daily caused improvement in the lens elasticity according to the increase of the duration of instillation, and showed definitely an improvement in lens elasticity after instillation for 3 days. This suggests that ursodeoxycholic acid can early cause the effect.

[Pharmacological Test 6]
The effect of once-daily instillation of ursodeoxycholic acid methyl ester for 7 days on the lens elasticity was examined.

(Preparation of Test Sample)
1) Preparation of Vehicle
A vehicle comprising 0.1% (w/v) of ethyl pyruvate, 0.269% (w/v) of sodium dihydrogenphosphate monohydrate ($NaH_2PO_4H_2O$), 0.433% (w/v) of disodium hydrogenphosphate ($Na_2HPO_4$), 0.2% (w/v) of hydroxypropyl methylcellulose, 0.5% (w/v) of NaCl was prepared.
2) Preparation of Ursodeoxycholic Acid Methyl Ester Sample
Ursodeoxycholic acid methyl ester was sonicated with the addition of the vehicle to prepare a 0.3% (w/v) suspension, a 1.0% (w/v) suspension and a 3.0% (w/v) suspension. The total amount of each sample to be used in one day was prepared before use.
(Test Method)
1) Each test sample (2.5 µL/eye) was instilled into both eyes of 7-month-old C57BL/6J mice with a Pipetman once per day (QD; around 13:30) for 7 days.
2) Twenty-four hours after the final instillation, the mice were euthanized by carbon dioxide inhalation, and then the eyeballs were extracted and rinsed with Hank's balanced salt solution (HBSS).
3) The sclera near the optic nerve was cut with a razor, the lens was removed through the incision, and the removed lens was immersed in HBSS.
4) The lens was placed on a glass slide, and an all-in-one fluorescence microscope BZ-9000 (Keyence) was used to capture an image of the lens (Image a).
5) Next, one cover glass (Corning® 22×22 mm Square) was placed on the lens, and an image in which the thickness of the lens changed due to the weight was similarly captured (Image b).
6) A change in the lens diameter was calculated from Equation 1 wherein the lens diameter of Image a is subtracted from the lens diameter of Image b, as described below. Then, the lens elasticity improvement of each sample group compared with the vehicle control group was calculated from Equation 2 described below. Each mean of the vehicle control group and each ursodeoxycholic acid methyl ester sample group was based on 9 or 10 eyes.

Change in lens diameter=Lens diameter in Image *b* of each test sample–Lens diameter in Image *a* of each test sample   (Equation 1)

Lens elasticity improvement of each sample group=Mean change in lens diameter of each Test sample group–Mean change in lens diameter of Vehicle control group   (Equation 2)

(Results)
The results are shown in Table 6.

TABLE 6

|  | Lens elasticity improvement (µm) |
|---|---|
| 0.3% ursodeoxycholic acid methyl ester sample | 13.2 |
| 1% ursodeoxycholic acid methyl ester sample | 33.0 |
| 3% ursodeoxycholic acid methyl ester sample | 46.5 |

As shown in Table 6, 1% ursodeoxycholic acid methyl ester sample and 3% ursodeoxycholic acid methyl ester sample caused a potent lens elasticity improvement even when they were instilled once-daily. These results suggest that ursodeoxycholic acid methyl ester may also have a more potent lens elasticity improvement effect compared with 1.5% EV06.

[Pharmacological Test 7]
The effect of tauroursodeoxycholic acid instilled once-daily for 7 days on the lens elasticity was examined.
(Preparation of Test Sample)
1) Preparation of Vehicle
A vehicle comprising 0.1% (w/v) of ethyl pyruvate, 0.269% (w/v) of sodium dihydrogenphosphate monohydrate ($NaH_2PO_4H_2O$), 0.433% (w/v) of disodium hydrogenphosphate ($Na_2HPO_4$), 0.2% (w/v) of hydroxypropyl methylcellulose, 0.5% (w/v) of NaCl was prepared.
2) Preparation of Tauroursodeoxycholic Acid Sample
Tauroursodeoxycholic acid was dissolved with the addition of the vehicle to prepare a 1.0% (w/v) solution. The total amount of each sample to be used in one day was prepared before use.
(Test Method)
1) Each test sample (2.5 µL/eye) was instilled into both eyes of 7-month-old C57BL/6J mice with a Pipetman once per day (QD; around 13:30) for 7 days.
2) Twenty-four hours after the final instillation, the mice were euthanized by carbon dioxide inhalation, and then the eyeballs were extracted and rinsed with Hank's balanced salt solution (HBSS).
3) The sclera near the optic nerve was cut with a razor, the lens was removed through the incision, and the removed lens was immersed in HBSS.
4) The lens was placed on a glass slide, and an all-in-one fluorescence microscope BZ-9000 (Keyence) was used to capture an image of the lens (Image a).
5) Next, one cover glass (Corning® 22×22 mm Square) was placed on the lens, and an image in which the thickness of the lens changed due to the weight was similarly captured (Image b).
6) A change in the lens diameter was calculated from Equation 1 wherein the lens diameter of Image a is subtracted from the lens diameter of Image b, as described below. Then, the lens elasticity improvement of each sample group compared with the vehicle control group was calculated from Equation 2 described below. Each mean of the vehicle control group and the tauroursodeoxycholic acid sample group was based on 10 eyes.

Change in lens diameter=Lens diameter in Image *b* of each test sample–Lens diameter in Image *a* of each test sample   (Equation 1)

Lens elasticity improvement of each sample group=Mean change in lens diameter of each Test sample group–Mean change in lens diameter of Vehicle control group   (Equation 2)

(Results)
The results are shown in Table 7.

TABLE 7

|  | Lens elasticity improvement (µm) |
|---|---|
| 1% tauroursodeoxycholic acid sample | 29.7 |

The 1% tauroursodeoxycholic acid sample instilled once-daily caused a potent lens elasticity improvement as shown in Table 7 while the 1.5% EV06 sample instilled once-daily for 14 days had no effect as shown in Table 4, which suggests that tauroursodeoxycholic acid has a more potent lens elasticity improvement effect than EV06.
[Pharmacological Test 8]
The effect of glycoursodeoxycholic acid instilled once-daily for 7 days on the lens elasticity was examined.

(Preparation of Test Sample)
1) Preparation of Vehicle
A vehicle comprising 0.1% (w/v) of ethyl pyruvate, 0.269% (w/v) of sodium dihydrogenphosphate monohydrate ($NaH_2PO_4H_2O$), 0.433% (w/v) of disodium hydrogenphosphate ($Na_2HPO_4$), 0.2% (w/v) of hydroxypropyl methylcellulose, 0.5% (w/v) of NaCl was prepared.
2) Preparation of Glycoursodeoxycholic Acid Sample
Glycoursodeoxycholic acid was sonicated with the addition of the vehicle to prepare a 1.0% (w/v) suspension. The total amount of each sample to be used in one day was prepared before use.
(Test method)
1) Each test sample (2.5 μL/eye) was instilled into both eyes of 8-month-old C57BL/6J mice with a Pipetman once per day (QD; around 13:30) for 7 days.
2) Twenty-four hours after the final instillation, the mice were euthanized by carbon dioxide inhalation, and then the eyeballs were extracted and rinsed with Hank's balanced salt solution (HBSS).
3) The sclera near the optic nerve was cut with a razor, the lens was removed through the incision, and the removed lens was immersed in HESS.
4) The lens was placed on a glass slide, and an all-in-one fluorescence microscope BZ-9000 (Keyence) was used to capture an image of the lens (Image a).
5) Next, one cover glass (Corning® 22×22 mm Square) was placed on the lens, and an image in which the thickness of the lens changed due to the weight was similarly captured (Image b).
6) A change in the lens diameter was calculated from Equation 1 wherein the lens diameter of Image a is subtracted from the lens diameter of Image b, as described below. Then, the lens elasticity improvement of each sample group compared with the vehicle control group was calculated from Equation 2 described below. Each mean of the vehicle control group and the glycoursodeoxycholic acid sample group was based on 9 to 10 eyes.

Change in lens diameter=Lens diameter in Image *b* of each test sample−Lens diameter in Image *a* of each test sample    (Equation 1)

Lens elasticity improvement of each sample group=Mean change in lens diameter of each Test sample group−Mean change in lens diameter of Vehicle control group    (Equation 2)

(Results)
The results are shown in Table 8.

TABLE 8

| | Lens elasticity improvement(μm) |
|---|---|
| 1% glycoursodeoxycholic acid sample | 20.1 |

The 1% glycoursodeoxycholic acid sample instilled once-daily caused a potent lens elasticity improvement as shown in Table 8 while the 1.5% EV06 sample instilled once-daily for 14 days had no effect as shown in Table 4, which suggests that glycoursodeoxycholic acid has a more potent lens elasticity improvement effect than EV06.
[Ocular Irritation Test]
(Preparation of Sample)
A vehicle (aqueous solution) comprising 0.1% (w/v) of ethyl pyruvate, 0.269% (w/v) of sodium dihydrogenphosphate.monohydrate ($NaH_2PO_4.H_2O$), 0.433% (w/v) of disodium hydrogenphosphate ($Na_2HPO_4$), 0.2% (w/v) of hydroxypropyl methylcellulose, 0.5% (w/v) of NaCl was prepared.
(Test Method)
Group treated with an ophthalmic suspension of ursodeoxycholic acid 1% (w/v), 3% (w/v), and 10% (w/v) ursodeoxycholic acid ophthalmic suspensions were prepared in the same manner as in the above pharmacological tests. These ophthalmic suspensions and the vehicle were each instilled into the left eye of Japanese White rabbits at a dose of 50 μL/eye with pipette twice per day at a 6-hour interval for 2 weeks. One hour after the final instillation, ocular irritation of anterior segment of the eye was evaluated according to the McDonald-Shadduck method, and the lens was observed. The contralateral eye was untreated.
The ocular irritation of anterior segment of the eye was scored according to the following criteria:
+1: mild; +2: moderate; +3: severe.
(Test Result)
The test results are shown in Table 9. After the 2 week-repeated instillation, no abnormal findings were observed in eyes treated with the ophthalmic suspensions of ursodeoxycholic acid in the observation of ocular irritation of anterior segment of the eye and lens observation. Histopathological examination of the eyes showed no abnormal findings.

TABLE 9

| Ophthalmic suspension | | Vehicle | 1% Ursodeoxycholic acid | 3% Ursodeoxycholic acid | 10% Ursodeoxycholic acid |
|---|---|---|---|---|---|
| Number of animals | | 3 | 3 | 3 | 3 |
| Ocular irritation of anterior segment of the eye [1] | Conjunctival hyperemia | — | — | — | — |
| | Palpebral conjunctival edema | — | — | — | — |
| | Discharge | — | — | — | — |
| | Corneal opacity | — | — | — | — |
| | Corneal epithelial disorder | — | — | — | — |
| Lens | | — | — | — | — |
| Histopathological examination | | — | — | — | — |

—: No noteworthy findings,
[1] Score of the instilled left eye and the number of the eye, 1 hour after the final instillation are described.

(Discussion)
It is shown that the ophthalmic suspensions of ursodeoxycholic acid is highly safe.

INDUSTRIAL APPLICABILITY

The agent of the present invention is useful for treating or preventing eye diseases such as presbyopia etc.

The invention claimed is:
1. A method for treating presbyopia, comprising administering to a subject in need thereof an effective amount of ursodeoxycholic acid, an amide conjugate of ursodeoxycholic acid, or an ester of ursodeoxycholic acid, or a pharmaceutically acceptable salt thereof, wherein the amide conjugate of ursodeoxycholic acid is an amide conjugate formed by dehydration condensation of the carboxyl group of ursodeoxycholic acid with an amino group of an amino compound selected from alanine, leucine, arginine, lysine, asparagine, methionine, aspartic acid, cysteine, glutamine, serine, glutamic acid, threonine, glycine, isoleucine, valine, 2-aminoadipic acid, 3-aminoadipic acid, 2-aminobutanoic acid, 4-aminobutanoic acid, 2,4-diaminobutanoic acid, 2-aminohexanoic acid, 6-aminohexanoic acid, β-alanine, 2-aminopentanoic acid, 2,3-diaminopropanoic acid, 2-aminopimelic acid, 2,6-diaminopimelic acid, cysteic acid, 2,4-diaminobutanoic acid, 2,6-diaminopimelic acid, 2,3-diaminopropanoic acid, 4-carboxyglutamic acid, homocysteine, homoserine, 5-hydroxylysine, allohydroxylysine, alloisoleucine, norleucine, norvaline, ornithine, allothreonine, and taurine; and the ester of ursodeoxycholic acid is an ester formed by dehydration condensation of the carboxyl group of ursodeoxycholic acid with a monohydric alcohol having 1 to 6 carbon atoms.

2. The method according to claim 1, wherein the ursodeoxycholic acid, an amide conjugate of ursodeoxycholic acid, or an ester of ursodeoxycholic acid, or a pharmaceutically acceptable salt thereof is administered ophthalmically.

3. The method according to claim 1, wherein the ursodeoxycholic acid, an amide conjugate of ursodeoxycholic acid, or an ester of ursodeoxycholic acid, or a pharmaceutically acceptable salt thereof is administered as an eye drop or an eye ointment.

4. The method according to claim 3, wherein the amount of ursodeoxycholic acid, an amide conjugate of ursodeoxycholic acid, or an ester of ursodeoxycholic acid, or a pharmaceutically acceptable salt thereof comprised in the eye drop or the eye ointment is 0.00001 to 10% (w/v).

5. The method according to claim 1, wherein the amide conjugate of ursodeoxycholic acid is an amide conjugate formed by dehydration condensation of the carboxyl group of ursodeoxycholic acid with an amino group of an amino compound selected from alanine, leucine, asparagine, methionine, aspartic acid, cysteine, serine, threonine, glycine, isoleucine, valine, 2-aminobutanoic acid, β-alanine, 2-aminopentanoic acid, 2,3-diaminopropanoic acid, cysteic acid, homocysteine, homoserine, alloisoleucine, norvaline, allothreonine, and taurine.

6. The method according to claim 1, wherein the ursodeoxycholic acid, an amide conjugate of ursodeoxycholic acid, or an ester of ursodeoxycholic acid, or a pharmaceutically acceptable salt thereof is selected from ursodeoxycholic acid, tauroursodeoxycholic acid, glycoursodeoxycholic acid, ursodeoxycholic acid methyl ester, ursodeoxycholic acid ethyl ester, ursodeoxycholic acid n-propyl ester, ursodeoxycholic acid isopropyl ester, ursodeoxycholic acid n-butyl ester, ursodeoxycholic acid isobutyl ester, ursodeoxycholic acid sec-butyl ester, ursodeoxycholic acid tert-butyl ester, ursodeoxycholic acid n-pentyl ester, ursodeoxycholic acid n-hexyl ester, and a pharmaceutically acceptable salt thereof.

7. The method according to claim 1, wherein the ursodeoxycholic acid, an amide conjugate of ursodeoxycholic acid, or an ester of ursodeoxycholic acid, or a pharmaceutically acceptable salt thereof is selected from ursodeoxycholic acid, tauroursodeoxycholic acid, glycoursodeoxycholic acid, ursodeoxycholic acid methyl ester, ursodeoxycholic acid ethyl ester, ursodeoxycholic acid n-propyl ester, ursodeoxycholic acid isopropyl ester, and a pharmaceutically acceptable salt thereof.

8. The method according to claim 1, wherein the ursodeoxycholic acid, an amide conjugate of ursodeoxycholic acid, or an ester of ursodeoxycholic acid, or a pharmaceutically acceptable salt thereof is ursodeoxycholic acid or a sodium salt thereof.

9. The method according to claim 3, wherein the eye drop or the eye ointment comprises water, and an additive selected from ethyl pyruvate, sodium dihydrogenphosphate monohydrate, disodium hydrogenphosphate, hydroxypropyl methylcellulose, NaCl, and a mixture thereof.

* * * * *

UNITED STATES PATENT AND TRADEMARK OFFICE
CERTIFICATE OF CORRECTION

| | |
|---|---|
| PATENT NO. | : 11,419,880 B2 |
| APPLICATION NO. | : 17/546895 |
| DATED | : August 23, 2022 |
| INVENTOR(S) | : Kato et al. |

It is certified that error appears in the above-identified patent and that said Letters Patent is hereby corrected as shown below:

On the Title Page

First column, below the section "(63) Related U.S. Application Data" and above the section "(51) Int. Cl.", add the following:
-- Foreign Application Priority Data
Dec. 18, 2018 (JP) ............... 2018-236717 --

Signed and Sealed this
First Day of November, 2022

Katherine Kelly Vidal
*Director of the United States Patent and Trademark Office*